United States Patent [19]

Chung et al.

[11] 3,984,490

[45] Oct. 5, 1976

[54] PHENYLCYCLOHEXANE FORMED BY CRACKING DICYCLOHEXYLBENZENE

[75] Inventors: Tae H. Chung; Chandrakant A. Patel, both of Wallingford; Adnan A. R. Sayigh, North Haven, all of Conn.

[73] Assignee: The Upjohn Company, Kalamazoo, Mich.

[22] Filed: May 8, 1975

[21] Appl. No.: 575,607

[52] U.S. Cl. .............................. 260/668 R; 260/667; 260/668 D
[51] Int. Cl.² ......................................... C07E 15/00
[58] Field of Search ............. 260/668 R, 668 D, 667

[56] References Cited
UNITED STATES PATENTS 2,839,590   6/1958   Fetterly........................... 260/668 D Primary Examiner—Veronica O'Keefe
Attorney, Agent, or Firm—Denis A. Firth; John Kekich

[57] ABSTRACT

A process is described for recovering phenylcyclohexane as principal product from dicyclohexylbenzenes by heating the latter in the presence of at least an equal amount by weight of benzene and an acid clay or zeolite catalyst at a temperature of 190° – 400°C. The period of heating is preferably controlled so that no significant cracking of the phenylcyclohexane is caused. The process is a useful adjunct to the known methods of production of phenylcyclohexane by hydrodimerization by benzene. The latter process gives significant amounts of dicyclohexylbenzenes as byproduct. The present process enables this generally undesirable by-product to be converted to phenylcyclohexane thus increasing the overall yield of phenylcyclohexane from benzene in the hydrodimerization process.

12 Claims, No Drawings

PHENYLCYCLOHEXANE FORMED BY CRACKING DICYCLOHEXYLBENZENE

BACKGROUND OF THE INVENTION

1. Field of the Invention

This invention relates to a process for the cracking of dicyclohexylbenzenes and is more particularly concerned with the catalytic cracking of dicyclohexylbenzenes to phenylcyclohexane.

2. Description of the Prior Art

Much attention has been paid to methods of synthesizing phenylcyclohexane which is an important intermediate in that it can be oxidized readily to a mixture of phenol and cyclohexanone. The latter compounds are widely used in the chemical industry as starting materials in a wide variety of syntheses.

A preferred route to phenylcyclohexane is through the catalytic hydrodimerization of benzene; see, for example, U.S. Pat. Nos. 3,317,611; 3,347,945; 3,412,165; 3,153,678; 3,274,276 and 3,829,514-7. However, the hydrodimerization product is generally found to contain significant quantities of dicyclohexylbenzenes, chiefly the m- and p-dicyclohexylbenzenes. It is highly desirable that the dicyclohexylbenzenes be utilized in some manner in order to improve the overall economics of the process. Unfortunately, there is little demand commercially for such products as intermediates in chemical synthesis.

I have now found that dicyclohexylbenzenes can be transformed in good yield to give phenylcyclohexane thereby adding significantly to the efficiency of the hydrodimerization process as a route to phenylcyclohexane.

SUMMARY OF THE INVENTION

This invention comprises a process for cracking dicyclohexylbenzenes to form phenylcyclohexane by heating said dicyclohexylbenzenes in the presence of at least an equal amount by weight of benzene and a catalyst selected from the class consisting of calcined acid clays and zeolites at a temperature in the range of 190° to 400°C.

DETAILED DESCRIPTION OF THE INVENTION

The dicyclohexylbenzenes which are cracked in accordance with the process of the invention can be the o-, m- or p-isomers individually or in the form of mixtures of two or more such isomers. In a particular embodiment of the process of the invention the crude mixture of dicyclohexylbenzenes, obtained as by-product in the preparation of phenylcyclohexane by hydrodimerization of benzene (see the art cited above), is employed as the starting material. The phenylcyclohexane thereby obtained serves to increase the overall yield in the conversion of benzene to phenylcyclohexane by hydrodimerization. Although it would be desirable for the sake of convenience to treat the crude reaction product from the hydrodimerization directly to convert the dicyclohexylbenzenes to phenylcyclohexane, it has been found in practice that it is not possible to do this without sacrifice of some yield of phenylcyclohexane. Accordingly, we prefer to isolate the dicyclohexylbenzenes from the hydrodimerization product before subjecting these compounds to the process of the invention.

In carrying out the process of the invention the dicyclohexylbenzene starting material is admixed with benzene in a proportion in the range of about 1 part by weight to about 10 parts by weight of benzene for each part by weight of dicyclohexylbenzene. Preferably the proportion is within the range of about 1.5 parts by weight to about 5 parts by weight of benzene for each part by weight of dicyclohexylbenzene.

The mixture of benzene and dicyclohexylbenzenes can be contacted with the catalyst in a batch type procedure or in a continuous procedure. In the batch type procedure the mixture of benzene and dicyclohexylbenzene is admixed with the catalyst and the resulting mixture is agitated and heated at a temperature in the range of about 190° to 400°C, preferably within a range of about 195°C to about 240°C. Advantageously the heating is carried out under an atmosphere of inert gas such as nitrogen, argon, krypton and the like and, preferably, at a pressure within the range of about 200 to 600 psig. Using the latter conditions, the reaction is carried out in the liquid phase thereby improving efficiency of operation and reducing the capacity of equipment required.

The progress of the reaction can be followed by appropriate analytical procedures. For example, an aliquot of the reaction mixture can be removed at selected intervals of time and subjected to spectroscopic examination such as by infra red and nuclear magnetic resonance spectroscopy or by gas chromatography. Disappearance of absorption bands corresponding to the dicyclohexylbenzene and/or appearance of bands corresponding to phenylcyclohexane provide means of checking the progress of the reaction.

It is important that the reaction time be maintained as short as possible since prolonged exposure of the phenylcyclohexane (produced in the reaction) to the reaction conditions can result in cracking of the latter compound to yield benzene and cyclohexene; see U.S. Pat. No. 2,839,590.

When the reaction is completed, as determined in the above manner, the desired phenylcyclohexane can be isolated from the reaction product by conventional procedures, for example, by fractional distillation, partition chromatography, and the like.

The proportion of catalyst employed in the above process is advantageously of the order of about 1 to about 30 parts by weight per 100 parts by weight of dicyclohexylbenzenes. Preferably the proportion of catalyst employed in the above process is within the range of about 10 to about 25 parts by weight per 100 parts by weight of dicyclohexylbenzenes.

In carrying out the process of the invention on a continuous basis various techniques can be employed. For example, the mixture of benzene and dicyclohexylbenzenes is passed, or allowed to flow, through a bed of the catalyst in a zone maintained at a temperature within the above range. The rate of flow of the reactants through the catalyst is adjusted so that the average residence time of the reactants in contact with the catalyst is of the same order as the time required for the reaction to reach completion under the particular conditions employed. The residence time is adjusted so that it is shorter than that required for any substantial amount of cracking of the phenylcyclohexane to occur; see supra. The appropriate residence time will obviously vary according to the particular combination of benzene proportion, reaction temperature and the like which is employed. The most appropriate residence time for any particular combination of conditions can be readily determined by a process of trial and error.

In an alternative manner of carrying out the process of the invention on a continuous basis a mixture of benzene, dicyclohexylbenzene and catalyst in the form of suspension is fed, for example by means of a pump or screwfeed, through a heating zone maintained within the range of temperature set forth above. The rate of flow is adjusted so that the average residence time in the heating zone conforms to the time required for the reaction to proceed to completion under the conditions employed. As set forth above, the residence time in any given instance is so chosen that no significant cracking of the phenylcyclohexane produced in the reaction will occur.

Other alternative ways in which the process of the invention can be carried out using conventional apparatus and techniques will be apparent to one skilled in the art.

The catalysts which are employed in the process of the invention can be any of the zeolites or acid clays, both of which materials are classes well-recognized in the art. By "acid" clay is meant a clay which, when suspended in water, exhibits a pH of less than 7.0. Preferably acid clays which give aqueous suspensions having a pH in the range of 1 to 6 are employed in the process of the invention. The clays meeting the above pH requirements include those which are acid in the natural state in which they are found as well as those which can be derived by washing a naturally occurring clay with a mineral acid in order to remove Na and Fe and or to adjust the pH to any predetermined level.

Advantageously, but not essentially, the clays employed in the process of the invention have been calcined, i.e. have been subjected to heating at temperatures of the order of about 300°C to about 500°C under atmospheric pressure, or at 100°C to 200°C under reduced pressure of the order of 50 mm of mercury or lower, in order to remove all traces of moisture, chemically bound or otherwise, therefrom.

Subject to the above considerations, any of the clays conventionally employed in the catalytic art can be employed in the process of the invention. Such clays include the naturally occurring and synthetic alumina silicates and are a well-recognized class of materials. Illustrative of the clays which, after acid treatment if necessary, and after calcination if desired, can be employed in the process of the invention are: Montmorillonitic clays including fuller's earth, bentonite, montmorillonite and the like; attapulgus clays; and kaolins.

A wide variety of such clays is available commercially. For example, kaolin clays in various particle sizes are available from the J. M. Huber Corporation, Huber, Ga. and from Air Products and Chemicals, Inc. Bentonite clays in a variety of grades are available under the trade name Filtrol from the Filtrol Corporation, Los Angeles, Calif. Montmorillonite clays mined in South Central Texas are available under the trade name Impact from The Milwhite Company, Houston, Texas.

A particularly preferred group of acid clays for use in the process of the invention are the bentonites available under the trade names Filtrol grades 13, 24 and 71.

The natural and synthetic zeolites, employed as catalysts in the process of the invention, are also a well-recognized class of materials. The synthetic zeolites are described, for example, in R. W. Grimshaw, The Chemistry and Physics of Clays, Fourth Edition Revised, 1971, p. 168–9, Ernest Benn Limited, London, and D. W. Breck, Zeolite Molecular Sieves, John Wiley & Sons, New York. The zeolites are hydrated alumino-silicates having a relatively open crystal lattice which can be readily synthesized and which can be subjected to cation exchange to produce forms having different cations. Any of these known zeolites in any of the different cation states can be employed in the process of the invention. The naturally occurring zeolites are sodium and calcium alumino silicates such as anocite, chabazite, heulandite, notrolite, stilbite and thomsonite; see, for example, Encyclopedia of Chemical Technology, Vol. 12, p. 295, 1954, Interscience Publishers, Inc., New York, New York. A particularly useful group of zeolites for use in the present invention are the rare earth exchanged zeolites of the types known as Types X and Y or the decationized zeolites of Types X and Y in the hydrogen form.

Advantageously, the acid clays or zeolites used for the batch reaction in stirred tank reactor are employed in powder form in the process of the invention. By this is meant that the average particle size of the acid clay or zeolite catalysts is advantageously below about 20 microns (or above 65 mesh). A number of the acid clays or zeolites are available in the form of pellets of various sizes, as extrudates, and as irregular granules, and such forms are particularly useful for continuous flow reactions according to the invention.

As set forth above, the process of the invention provides a relatively simple and economical method of recovering phenylcyclohexane from dicyclohexylbenzenes. The process is particularly valuable when used in conjunction with the process of preparing phenylcyclohexane by hydrodimerization of benzene since it provides a means of obtaining additional quantities of phenylcyclohexane from the otherwise useless by-product, dicyclohexylbenzenes, formed in the hydrodimerization reaction. The finding that the process of the invention can be operated successfully is very surprising in view of the report in the literature (U.S. Pat. No. 2,839,590) discussed above that phenylcyclohexane will itself undergo cracking to benzene and cyclohexane when subjected to heating in the presence of certain clays.

The following examples describe the manner and process of making and using the invention and set forth the best mode contemplated by the inventors of carrying out the invention but are not to be construed as limiting.

EXAMPLE 1

The dicyclohexylbenzene employed as starting material was a mixture containing 52.3% m-dicyclohexylbenzene, 44.8% p-dicyclohexylbenzene, the remainder (2.9%) being unknown which mixture had been obtained by distillation of the product of the following hydrodimerization reaction:

A total of 1700 g. of molecular sieve (Linde 13x) treated benzene was charged to a .1 gallon autoclave containing 339.4 g. of 3.6% NiREY zeolite matrix (Grace XZ-25 zeolite matrix fluid cracking catalyst loaded with nickel) which had been used 8 times previously for the same purpose. The autoclave was pressured to 150 psig with $H_2$ and heated to 190°C. Then, it was pressured to 450 psig by opening the pre-set hydrogen pressure regulator, at which moment the temperature rose quickly to over 200°C. The temperature was automatically maintained at 200°–208°C. In 36 minutes, 930 psi of $H_2$ was used up and the hydrogen valve was closed and the autoclave was cooled rapidly.

A gas chromatography analysis indicated that the conversion of benzene was 33.1% and selectivities to phenylcyclohexane, cyclohexane and m- and p-dicyclohexylbenzenes were 64.2, 18.4, 3.3 and 3.3%, respectively.

The product was fractionally distilled to recover phenylcyclohexane and the aforesaid fraction containing dicyclohexylbenzenes.

The cracking of the dicyclohexylbenzenes was carried out as follows:

A mixture of 34.8 g. of benzene and 17.4 g. of the above dicyclohexylbenzene mixture was stirred under nitrogen with 3.5 g. of bentonite clay (pH ca 3.5: Filtrol 13: Filtrol Corporation, Los Angeles, California) which had previously been calcined for 12 hrs. at 160°C under vacuum. The mixture was heated with stirring for 2 hrs. at a temperature of 200° to 222°C before being cooled and filtered. The filtrate was found by vapor phase chromatography to have the following composition:

|  | % by wt. |
| --- | --- |
| benzene | 63.6 |
| phenylcyclohexane | 25.2 |
| m-dicyclohexylbenzene | 5.6 |
| p-dicyclohexylbenzene | 2.8 |
| methylcyclopentane | 0.6 |
| other unidentified material | 2.2 |

The above indicates a 98% selectivity in the conversion of dicyclohexylbenzenes to phenylcyclohexane and 72.1% conversion of dicyclohexylbenzenes to phenylcyclohexane.

EXAMPLE 2

The dicyclohexylbenzenes starting material emloyed in the following process was a mixture obtained by distilling the reaction product obtained by hydrodimerization of benzene using the same procedure as that described in the beginning of Example 1, and collecting the fraction having a boiling point of 164 to 165°C at a pressure of 0.08 mm. of mercury absolute. The mixture contained 53.8% by weight of m-dicyclohexylbenzene and 37.6% by weight of p-dicyclohexylbenzene, the remainder (8.6% by weight) being of unknown composition. The dicyclohexylbenzenes fraction was mixed with twice its own weight of benzene (previously dried over molecular sieves) and was treated as described below.

The catalyst employed in the following process was Filtrol Grade 24 (a bentonite clay, acid activated, pH 3.0 20–60 mesh; Filtrol Corporation).

The apparatus employed comprised an open system having a ½ inch o.d. tubular reactor mounted vertically and having 50 g. of the above catalyst supported therein. The benzene solution of dicyclohexylbenzene was stored in a vessel and pumped via a preheater to the base of the tubular reactor. Treated material was conducted from the top of the reactor through a cooling zone to a product storage vessel. The whole system was pressurized with nitrogen at 300–310 psig and maintained thereat throughout the procedure. The temperature of the reactor and contents was maintained at approximately 204°–214°C. The benzene solution of dicyclohexylbenzenes was passed through the reactor at an average liquid hourly space velocity (LHSV) of 0.35, and the operation was carried out continuously for a total period of 9.4 hours (total benzene solution processed in this time = 310 g.). Sample analyses of the product were made at 1.4, 8.1 and 9.4 hours. The reaction conditions and results achieved at the above three sample times were as follows:

| Sample Time (hr.) | Temp. °C | Press. psig. | LHSV hr.$^{-1}$ | % Conversion | Selectivity |
| --- | --- | --- | --- | --- | --- |
| 1.4 | 214 | 300 | 0.200 | 94.6 | 51.0 |
| 8.1 | 207 | 310 | 0.346 | 80.8 | 90.9 |
| 9.4 | 204 | 310 | 0.369 | 82.5 | 90.3 |

EXAMPLE 3

The dicyclohexylbenzenes starting material employed in the following process was obtained by fractional distillation of the product from a hydrodimerization of benzene carried out in accordance with the procedure described at the beginning of Example 1. The dicyclohexylbenzenes fraction, boiling point 164°–165°C at 0.08 mm of mercury, contained 54.3% m-dicyclohexylbenzene and 38.2% p-dicyclohexylbenzene by weight.

A solution of 20 g. of the above mixture of dicyclohexylbenzenes in 40 g. of benzene (previously dried over molecular sieves) was charged to a 310 ml. Parr bomb together with 4 g. of REX zeolite matrix (Grace X2-25 12–20 mesh having typical chemical analysis of $Al_2O_3$, 31.4; $SiO_2$, 56; $Na_2O$, 0.5; Fe, 0.09; previously heated at 500°C for 2.5 hours). The reactor was purged with nitrogen, pressured to 300 psig and heated to 215°C with agitation. After maintaining the reaction mixture at 216° – 218°C for 1 hour with agitation, the reactor was cooled rapidly to circa 20°C and the product removed. The latter was found, by gas chromatography, to contain 67.41% benzene, 25.47% phenylcyclohexane, 2.1% m-dicyclohexylbenzene and 1.46% p-dicyclohexylbenzene. The selectivity was 98.5% and conversion 84%.

We claim:

1. A process for cracking dicyclohexylbenzenes to form phenylcyclohexane which comprises heating said dicyclohexylbenzenes in admixture with at least an equal amount by weight of benzene in the presence of a catalyst consisting essentially of a member selected from the class consisting of calcined acid clays and zeolites and at a temperature in the range of 190° to 400°C.

2. A process according to claim 1 wherein the catalyst is a bentonite clay.

3. A process according to claim 1 wherein the catalyst is a rare earth exchanged zeolite type X resin.

4. A process according to claim 1 wherein the dicyclohexylbenzenes are a crude mixture recovered from the reaction product obtained in the catalytic hydrodimerization of benzene.

5. A process according to claim 1 wherein the reaction is carried out under pressure in the liquid phase in an atmosphere of nitrogen.

6. A process for cracking dicyclohexylbenzenes to form phenylcyclohexane which comprises passing a feed mixture of dicyclohexylbenzene and at least an equal amount by weight of benzene in the liquid phase through a column of catalyst consisting essentially of a member selected from the class consisting of calcined acid clays and zeolites at a temperature of 190° to 400°C 7. The process of claim 6 wherein the average residence time of said feed mixture in said column of catalyst is less than that required to effect substantial further cracking of the phenylcyclohexane which is produced by cracking of the dicyclohexylbenzenes.

8. The process of claim 6 wherein the reaction is carried out in an atmosphere of nitrogen at a pressure sufficient to maintain said feed mixture in the liquid phase.

9. The process of claim 6 wherein the catalyst is a bentonite clay.

10. The process of claim 6 wherein the catalyst is a rare earth exchanged zeolite type X resin.

11. The process of claim 6 wherein the dicyclohexylbenzenes employed in said feed mixture are a crude mixture recovered from the reaction product obtained in the catalytic hydrodimerization of benzene.

12. The process of claim 6 wherein the reaction temperature is within the range of 195°C to 240°C.

* * * * *